(12) United States Patent
Bruneau et al.

(10) Patent No.: US 6,579,298 B1
(45) Date of Patent: Jun. 17, 2003

(54) METHOD AND APPARATUS FOR TREATING VEIN GRAFT LESIONS

(75) Inventors: Rodney J. Bruneau, Kirkland, WA (US); Robert L. Barry, Kirkland, WA (US); Tim J. Johnson, Seatac, WA (US); Casey Torrance, Seattle, WA (US); Dennis Werner, Redmond, WA (US); Andy Uhrberg, Monroe, WA (US); Matthew Hefner, Puyallup, WA (US); Zihong Guo, Bellevue, WA (US); Mark Wyzgala, Bellevue, WA (US); Robert Morey, Redmond, WA (US); Natalya Peskin, Redmond, WA (US); Brian T. Cran, Seattle, WA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/514,664

(22) Filed: Feb. 29, 2000

(51) Int. Cl.[7] .......................... A61B 17/22; A61B 17/14
(52) U.S. Cl. ........................................ 606/159; 606/180
(58) Field of Search ...................... 606/1, 159, 170, 606/171, 180, 20, 85, 161, 167; 604/22

(56) References Cited

U.S. PATENT DOCUMENTS

| | | | | |
|---|---|---|---|---|
| 3,886,943 A | * | 6/1975 | Skiff et al. .................. 128/305 |
| 3,937,222 A | | 2/1976 | Banko | |
| 4,679,558 A | | 7/1987 | Kensey et al. | |
| 4,686,982 A | | 8/1987 | Nash | |
| 4,746,376 A | | 5/1988 | Bessey | |
| 4,747,821 A | | 5/1988 | Kensey et al. | |
| 4,751,922 A | * | 6/1988 | DiPietropolo ................ 606/80 |
| 4,857,046 A | | 8/1989 | Stevens et al. | |
| 5,042,984 A | | 8/1991 | Kensey et al. | |
| 5,097,849 A | | 3/1992 | Kensey et al. | |
| 5,395,311 A | | 3/1995 | Andrews | |
| 5,507,761 A | | 4/1996 | Duer | |
| 5,512,044 A | | 4/1996 | Duer | |
| 5,643,298 A | | 7/1997 | Nordgren et al. | |
| 5,676,545 A | * | 10/1997 | Jones ......................... 433/165 |
| 5,681,336 A | | 10/1997 | Clement et al. | |
| 5,690,634 A | * | 11/1997 | Muller et al. .................. 606/80 |
| 5,755,718 A | * | 5/1998 | Sklar .......................... 606/170 |
| 5,759,185 A | * | 6/1998 | Grinberg ...................... 606/80 |
| 5,779,721 A | | 7/1998 | Nash | |
| 5,857,995 A | * | 1/1999 | Thomas et al. ............... 604/22 |
| 5,865,794 A | | 2/1999 | Castro | |
| 5,879,361 A | | 3/1999 | Nash | |
| 5,899,908 A | * | 5/1999 | Kuslich et al. ............... 606/96 |
| 5,913,867 A | * | 6/1999 | Dion .......................... 606/180 |
| 5,922,022 A | | 7/1999 | Nash et al. | |
| 6,030,401 A | * | 2/2000 | Marino ....................... 606/180 |
| 6,053,923 A | * | 4/2000 | Veca et al. .................... 606/80 |
| 6,066,149 A | * | 5/2000 | Samson et al. ............. 606/159 |
| 6,126,667 A | * | 10/2000 | Barry et al. ................. 606/159 |
| 6,146,395 A | * | 11/2000 | Kanz et al. ................. 606/159 |
| 6,156,048 A | * | 12/2000 | Wulfman et al. ........... 606/159 |
| 6,206,898 B1 | * | 3/2001 | Honeycutt et al. .......... 606/159 |
| 6,235,035 B1 | * | 5/2001 | Boukhris ...................... 606/80 |
| 6,258,093 B1 | * | 7/2001 | Edwards et al. .............. 606/80 |
| 6,328,750 B1 | * | 12/2001 | Berry et al. ................ 606/168 |
| 6,416,526 B1 | * | 7/2002 | Wyzgala et al. ............ 606/170 |

* cited by examiner

*Primary Examiner*—Sharon Kennedy
(74) *Attorney, Agent, or Firm*—Christensen O'Connor Johnson Kindness PLLC

(57) ABSTRACT

A system for ablating material in vein grafts includes an ablation burr that is rotated by a driveshaft. The ablation burr preferably includes one or more channels, blades or other mechanisms that direct ablated material and liquid proximally and/or outwardly against a vessel wall. Aspiration is used to remove ablated material and liquid from the treatment area. Finally, methods for treating vein grafts and original native arteries are disclosed.

4 Claims, 15 Drawing Sheets

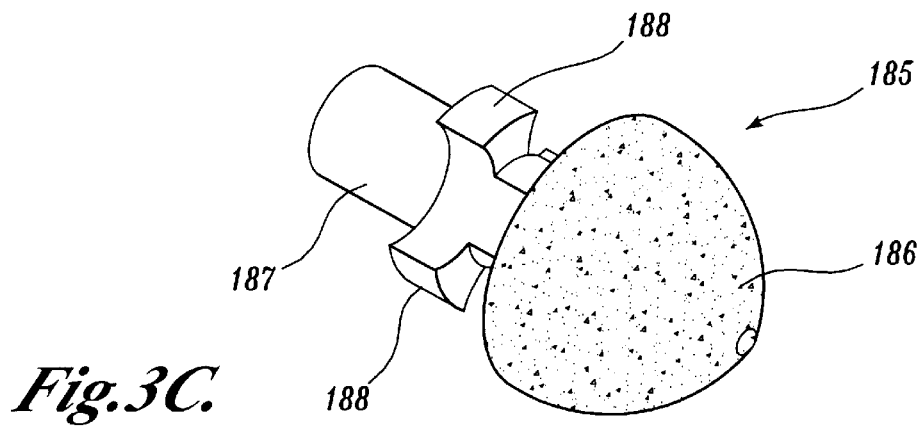
*Fig.3C.*
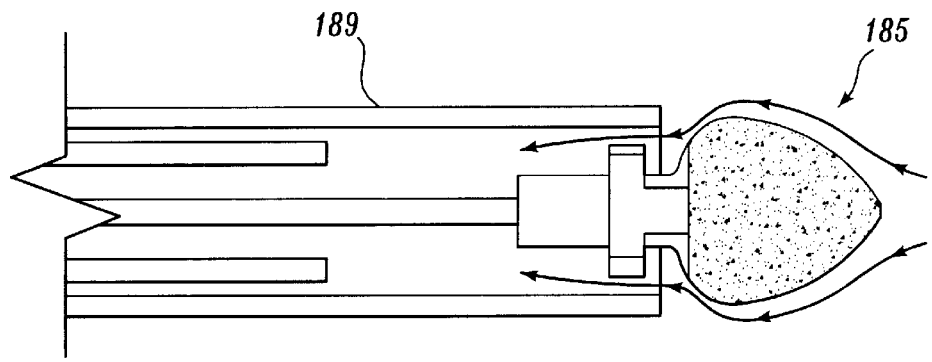
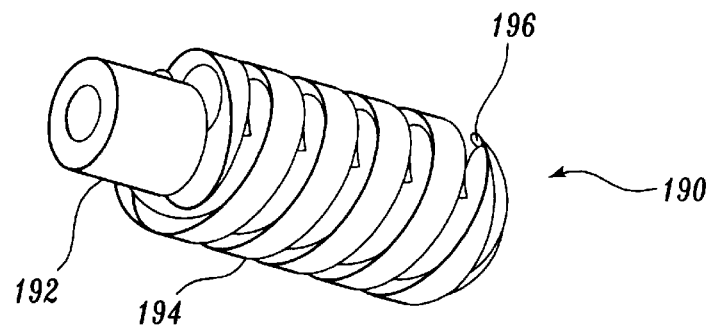
*Fig.4.*

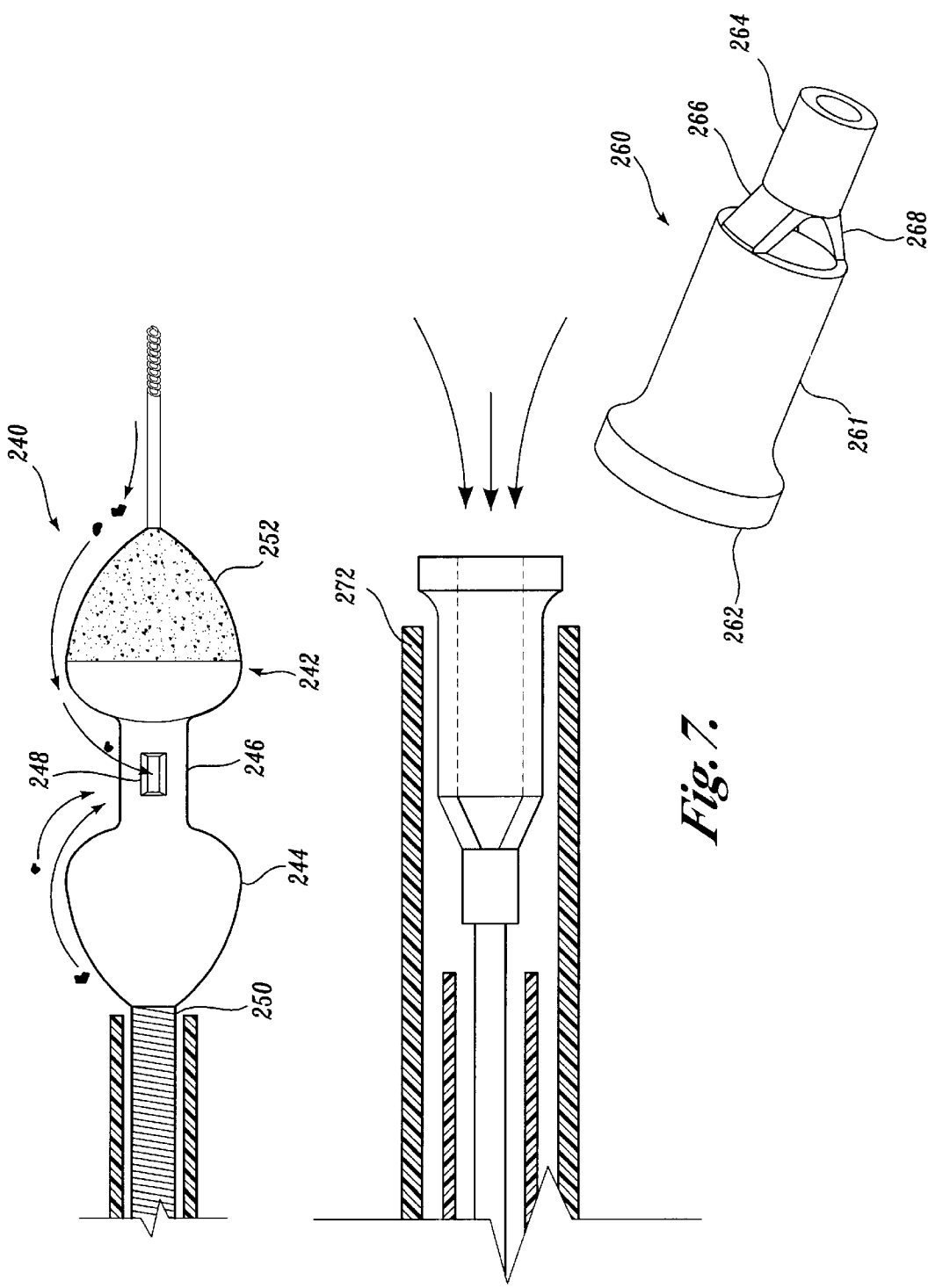

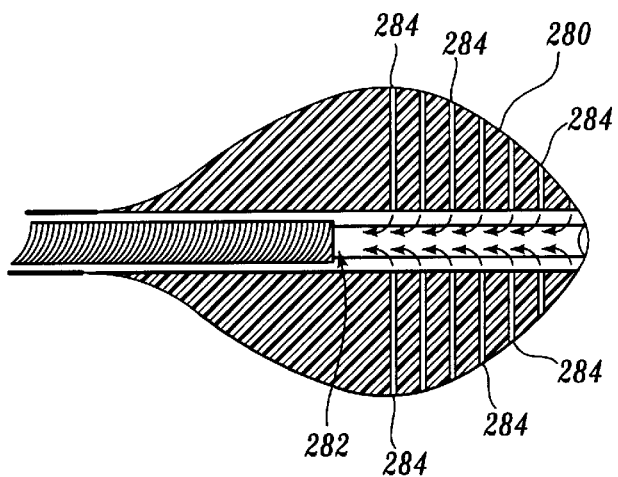
*Fig. 8A.*
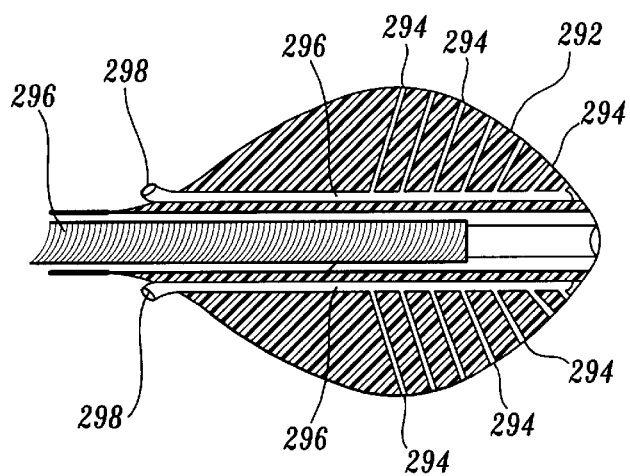
*Fig. 8B.*

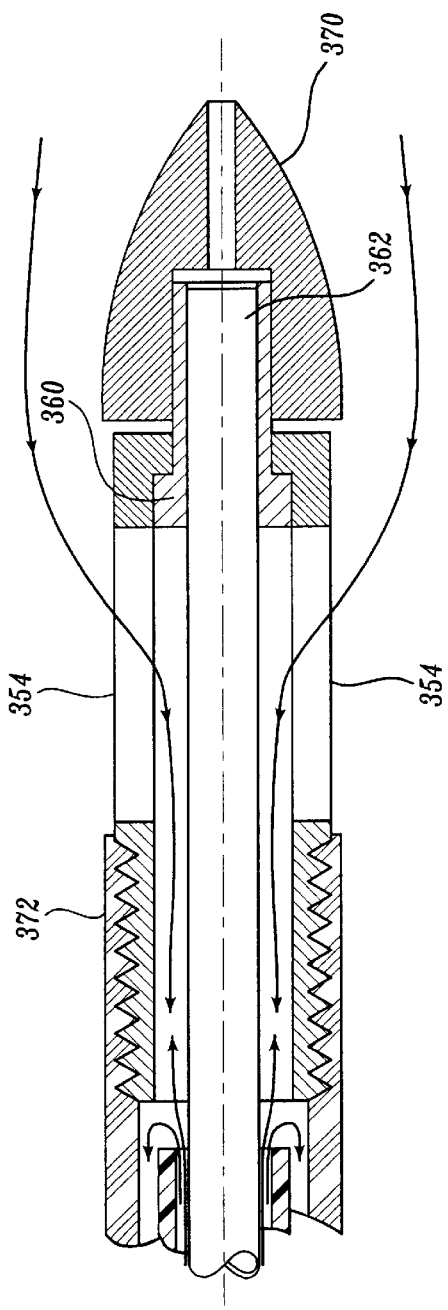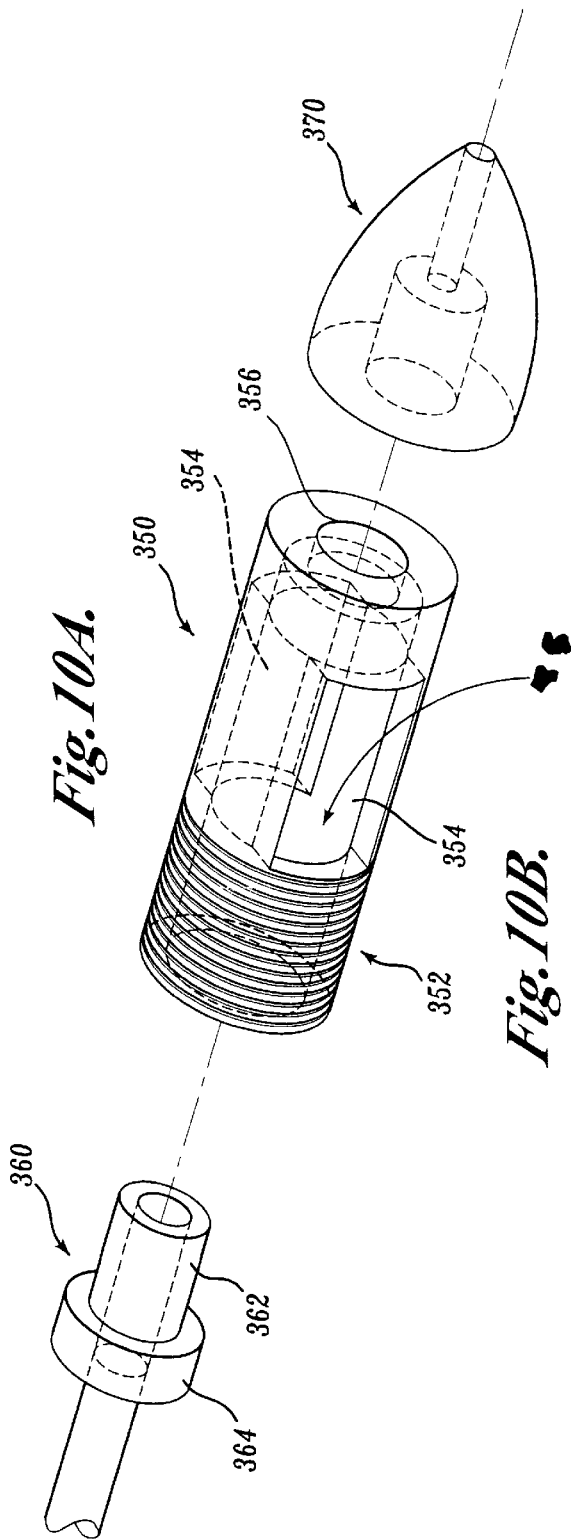

METHOD AND APPARATUS FOR TREATING VEIN GRAFT LESIONS

FIELD OF THE INVENTION

The present invention relates to medical devices in general, and in particular to catheter ablation systems for revascularizing occluded vein grafts.

BACKGROUND OF THE INVENTION

One of the most commonly used techniques for treating partially or totally occluded cardiac vessels is cardiac bypass surgery. With this procedure, a surgeon obtains a vessel from another portion of the patient's body and grafts the new vessel to healthy sites in the cardiac vessels in order to direct blood flow around a blockage. One of the most common vessels used in bypass surgery is a portion of the saphenous vein, which is a large superficial vein found in the leg. Such grafts are often referred to as saphenous vein grafts or SVGs.

One of the problems with SVGs is that they also tend to become occluded within three to five years of being grafted onto the heart muscle. For some physiological reason which is not completely understood, the material that occludes such grafts tends to be more loosely organized and brittle than the material that occludes native cardiac arteries. As a consequence, treating occluded SVGs can be more difficult because the occluding material tends to break off and can flow downstream wherein it may cause the onset of a heart attack.

One method of treating vein graft lesions is set forth in U.S. Pat. No. 5,681,336 to Clement et al. and assigned to the assignee of the present invention. The '336 patent, which is herein incorporated by reference, discloses a system of ablating vein graft lesions including proximal and distal balloons that isolate the treatment area. In addition, the system provides for the aspiration of ablated material and/or infusion of liquids to maintain vascular pressure. In the '336 patent, the ablation burrs are designed to abrade a lesion in the vein wherein the abraded material can be aspirated through a catheter that extends into the treatment area.

While it is believed that the system described in the '336 patent works well, additional benefits may be obtained using ablation burrs that are optimized for particle aspiration and removal of the type of blocking material found in saphenous vein grafts.

SUMMARY OF THE INVENTION

To improve the treatment of occluded saphenous vein grafts, the present invention comprises a system for aiding in the aspiration of ablated material from a vessel. The system includes a guide wire which is advanced into a treatment area and an ablation mechanism that is routed over the guide wire. The ablation mechanism includes an ablation burr that is rotated by a driveshaft, and a hollow sheath that extends over the driveshaft. The position of the guide wire and ablation mechanism are controlled by an advancer that moves these elements within a patient's vasculature. Rotation of the driveshaft is controlled by a prime mover, typically an electric motor or air turbine. The guide wire, driveshaft and sheath extend through a Y connector. One port of the Y connector is connected to a vacuum source that draws ablated material into a collection jar. The other port of the Y connector is coupled to the advancer.

According to one aspect of the present invention, an ablation burr is designed to propel ablated material proximally into an aspiration lumen. The ablation burr includes one or more channels on the surface of the burr that direct ablated material and fluid in the vessel to the aspiration lumen as the burr is rotated. In another embodiment of the invention, the one or more channels on the burr direct fluid and ablated material and fluid in the vessel proximally and radially outward to provide a scouring action of the interior vascular wall.

In accordance with another aspect of the invention, an ablation burr has a proximal and distal section with the distal section having a point of maximum diameter where the proximal and distal sections meet. The diameter of the distal section tapers down to a distal tip of the burr such that the distal section is ovoidal in shape. The distal section includes one or more channels that direct ablated material and fluid towards an aspiration lumen and/or toward the interior vascular wall. The proximal section comprises a cylindrical tube of a smaller diameter than the maximum diameter of the burr. The cylindrical tube may include one or more spiral channels that direct ablated material toward an aspiration lumen. In accordance with another aspect of the invention, the distal section has a diameter that decreases linearly from the point of maximum diameter to the distal tip such that the distal section of the burr has a conical configuration.

In accordance with another aspect of the present invention, an ablation burr has a diameter that tapers between the point of maximum diameter and the point where the distal section of the burr joins the proximal section. This tapered section includes a number of channels that direct fluids and ablated material towards the interior vascular wall to provide a scouring action in the vessel.

In accordance with another aspect of the present invention, the atherectomy burr fits within a protective shroud. The atherectomy burr has a relatively flat distal face that is covered with an abrasive material. The burr has one or more tapered blades that extend proximally from the distal face that move the ablated material and liquid proximally as the burr rotates.

In accordance with another aspect of the invention, the ablation burr comprises an auger-type bit that cuts occluding material from the vessel and moves it proximally to an aspiration lumen.

In accordance with another aspect of the present invention, the ablation burr is designed as a hub of cutting blades that fit within a canister. The blades are joined at the center of the burr and extend radially outward from a central axis to the inner wall of the canister. A central lumen extends through the point at which the blades are joined so the burr can be passed over a guide wire. Each of the blades includes a tab that fits into a corresponding slot on the canister to secure the blades in the canister.

In accordance with yet another aspect of the present invention, the ablation burr has a "dumbbell" shape having proximal and distal radially expanded portions. Each of the expanded portions moves liquid and abraded material radially outward as the burr is rotated. An aperture positioned between the distal and proximal radially expanded portions is in an area of low pressure so that the aperture acts as an aspiration port to aspirate material through a driveshaft that rotates the burr.

In accordance with yet another aspect of the present invention, the ablation burr has a bell shape with a large central lumen that is expanded at the distal end. A distal rim of the burr is covered with an abrasive material. The central lumen of the burr allows abraded material to be gathered and directed proximally to an aspiration sheath that is positioned near the proximal end of the burr and in fluid communication with the central lumen.

In accordance with yet another aspect of the present invention, the ablation burr includes a series of radial holes that extend into a center lumen of the burr. A vacuum is applied to the center lumen such that occluding material in the vessels is drawn into one or more holes and is sheared off the vessel wall by rotation of the burr. The ablated material may flow through the holes and into the center lumen of the burr where it is aspirated out a center of a driveshaft or may be drawn over the burr into another aspiration lumen.

In accordance with another aspect of the invention, the plurality of holes are coupled to one or more fittings that mate with corresponding lumens in a catheter sheath. The additional lumens are used to aspirate ablated material drawn into the holes and to provide vacuum pressure.

In accordance with yet another aspect of the present invention, an ablation device comprises an outer shell having an abrasive leading surface and a core that fits within the outer shell. Liquid and material disposed between the core and the inner surface of the shell are propelled proximally by the rotation of the core and shell.

In accordance with yet another aspect of the present invention, the ablation burr is maintained at a fixed distance from the distal end of a sheath by a coupler having a threaded end that mates with threads on the distal end of the sheath. The ablation burr is secured to the coupler via a post having a proximal cap with a diameter that is larger than the diameter of a hole at the distal end of the coupler.

The post also includes a distal shaft to which the ablation burr is secured. In accordance with yet another aspect of the invention, an ablation burr includes one or more holes that eject fluid that pumped through a sealed driveshaft radially outward to scour the internal vessel walls in which the burr is being used.

In accordance with yet another aspect of the present invention, a driveshaft that rotates an ablation burr includes a conically shaped section at its distal end. Fluid entering the space between the conically shaped section of the driveshaft and a surrounding sheath is pushed radially outward and proximally by the rotation of the driveshaft thereby aiding in the aspiration of ablated material and liquid from a vessel.

In accordance with yet another aspect of the invention, an expandable sleeve fits within the sheath surrounding the driveshaft. During an ablation procedure, the sheath is extended from the distal end of the sheath and expands to seal the proximal portion of the treatment site and to aid in the aspiration of material from the vessel.

In accordance with yet another aspect of the invention, a method is disclosed for isolating a treatment area by routing a catheter having an inflatable balloon through a native coronary artery to the point where a bypass vessel is attached to the native artery. The balloon is inflated to seal the bypass artery so that ablation can take place without ablated material being pumped downstream.

Finally, the present invention is a method for treating occluded native arteries by routing a catheter having an inflatable balloon through a bypass vessel and into the native artery in order to seal a treatment area such that the original blockage in the native artery can be ablated.

BRIEF DESCRIPTION OF THE DRAWINGS

The foregoing aspects and many of the attendant advantages of this invention will become more readily. appreciated as the same become better understood by reference to the following detailed description, when taken in conjunction with the accompanying drawings, wherein:

FIG. 3C illustrates an alternative ablation burr having a convention ellipsoidal distal portion and blades on a proximal portion that move ablated material and fluid proximally when rotated;

FIG. 4 illustrates an auger-type ablation burr that moves ablated material proximally when rotated in accordance with another aspect of the present invention;

FIG. 6 illustrates a "dumbbell"-shaped burr in accordance with another aspect of the present invention;

FIG. 7 illustrates a "bell"-shaped ablation burr in accordance with yet another aspect of the present invention;

FIGS. 8A–8B illustrate an ablation burr having multiple suction ports in its outer surface in accordance with yet another aspect of the present invention;

FIGS. 10A–10B illustrate a coupler that maintains the distance between an ablation burr and an aspirating sheath catheter in accordance with another aspect of the present invention;

DETAILED DESCRIPTION OF THE PREFERRED EMBODIMENT

Figure 1:
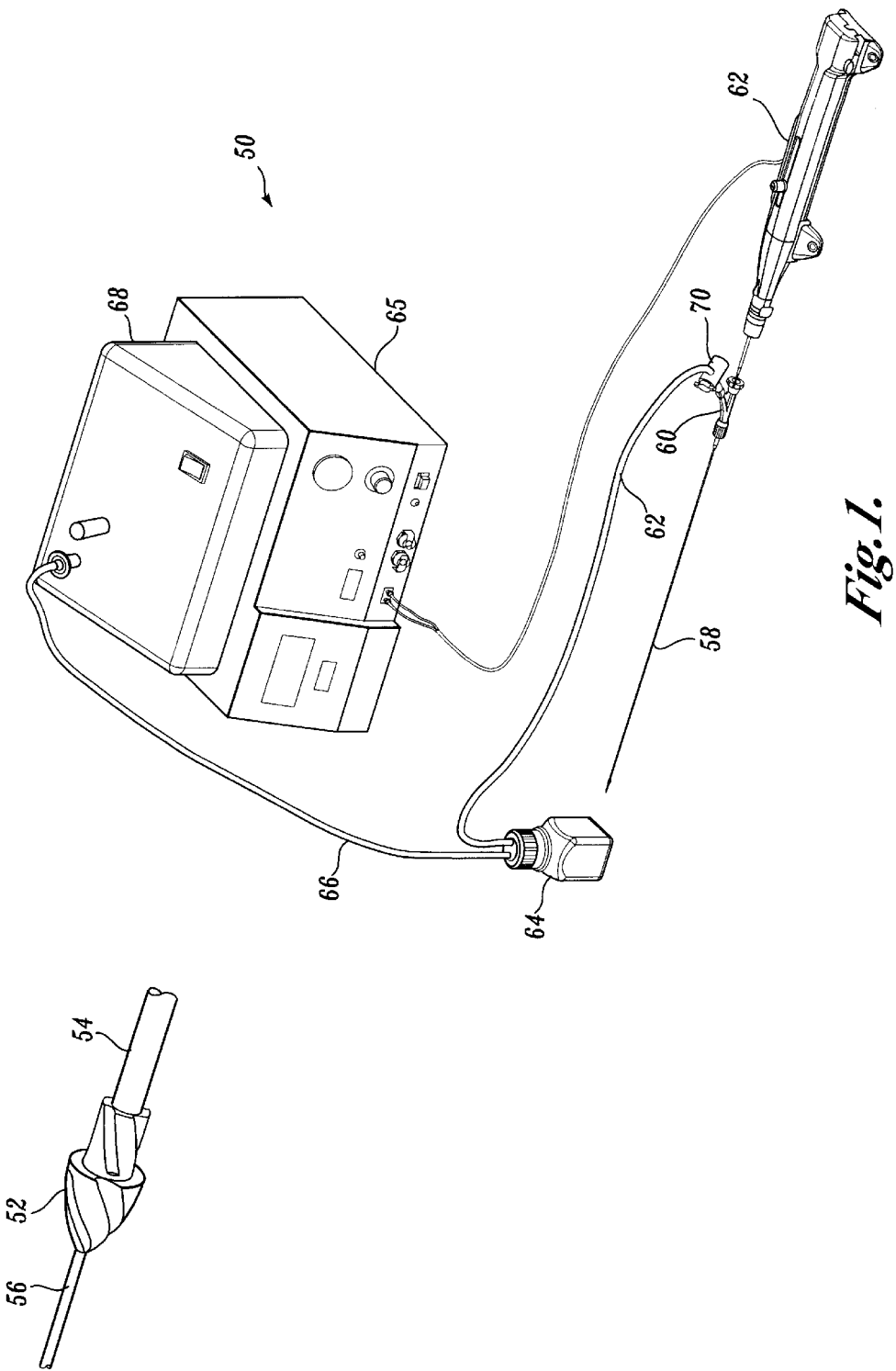
FIG. 1 illustrates a system for treating blockages in vein graft according to a currently preferred embodiment of the invention.

FIG. 1 illustrates a system for treating total or partial occlusions in vein grafts according to one embodiment of the present invention. The system 50 includes an ablation burr 52 that is rotated by a driveshaft 54. The ablation burr 52 and driveshaft 54 are threaded over a guide wire 56. The majority of the driveshaft 54 is covered by a sheath 58. The guide wire 56, driveshaft 54 and sheath 58 extend through a port in a Y connector 60 to an advancing mechanism 62. The advancing mechanism 62 is used to advance the driveshaft 54 over the guide wire 56 during treatment of a bypass vein graft. In the presently preferred embodiment of the invention, the driveshaft is rotated by an air turbine (not shown) within the advancer 62. The speed of the turbine is controlled by pressurized air that is regulated by a controller 65 in order to maintain the speed of rotation of the turbine in a desired range.

The Y connector 60 also has a port coupled to a vacuum tube 62 that is in line with a collection jar 64. A tube 66 connects the collection jar 64 with a vacuum source 68. The vacuum source 68 applies suction through the vacuum tube 62 and the tube 66 to the sheath 58 that surrounds the driveshaft 54 in order to aspirate ablated material from a treatment area in the patient's body. A valve 70 that is in line with the vacuum tube 62 provides manual control of the level of aspiration at the treatment site.

In operation, a physician makes an incision in the patient, typically in the femoral artery, and routes the guide wire 56 through the patient's vasculature to a point near the occluded vessel. Next, a guide catheter is routed over the guide wire to a point just proximal to the occlusion. The ablation burr 52 and driveshaft 54 are then routed over the guide wire 56 to the point of the occlusion. In some instances, it may be desirable to isolate the treatment area on either side of the occlusion using distal and proximal balloons as disclosed in the '336 patent referenced above.

Once the treatment area is isolated, the driveshaft is rotated at a relatively high speed as controlled by the controller 65. The physician advances the ablation burr using the advancer 62 such that the ablation burr 52 passes through the occluding material. Abraded material is collected in the collection jar 64 by the vacuum source 68.

By viewing the debris collected in the collection jar 64, the physician can determine whether more or less aspiration is required which can be adjusted using the valve 70. To prevent possible vessel collapse, fluid aspirated from the treatment site should be balanced with fluid infused to the treatment site. Therefore an infusion catheter may be included with the system to replace an amount of fluid equivalent to the amount that is aspirated. Flow meters on the vacuum lines and the infusion catheters may be provided to aid in balancing the infusion/aspiration rates. In addition, a pressure transducer may be positioned at the treatment site to aid in balancing fluid infusion/aspiration.

Once the ablation burr 52 has passed through the occlusion and the treatment is complete, the ablation burr 52, driveshaft 54 and guide wire 56 are removed from the patient followed by the guide catheter.

Figure 2A:
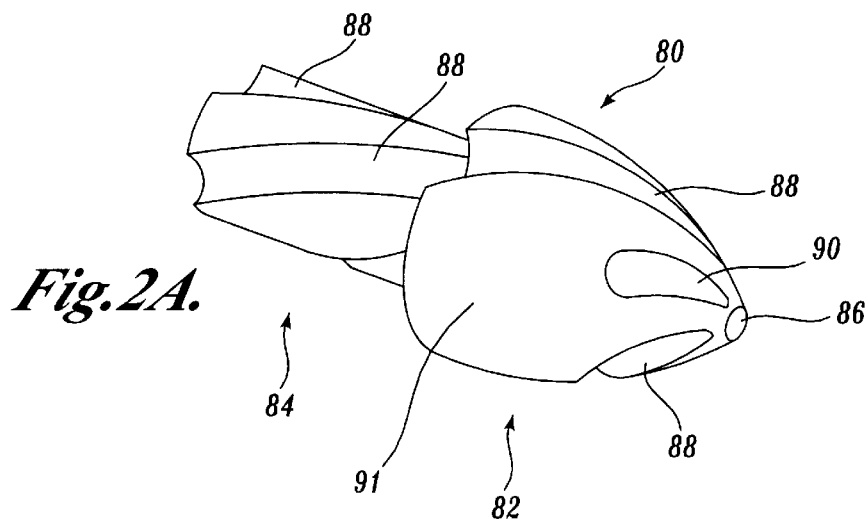
FIGS. 2A–2C illustration alternative ablation burrs constructed in accordance with various aspects of the present invention.
Figure 2B:
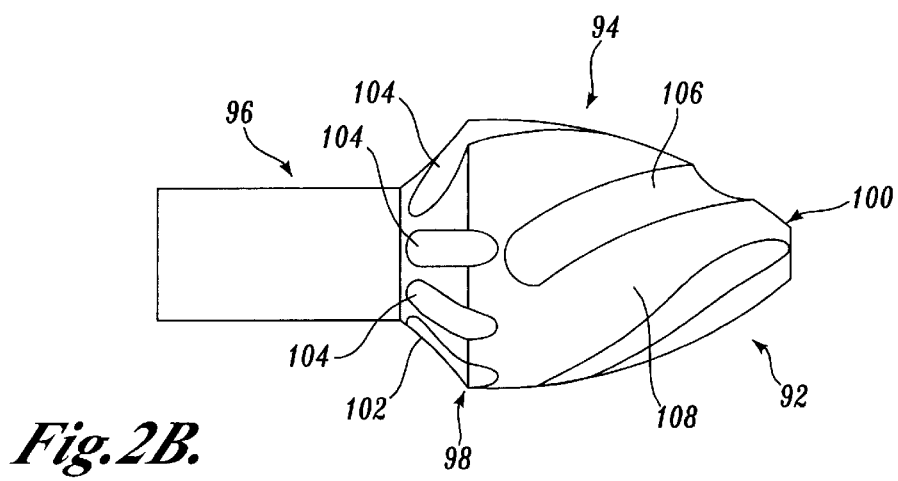
Figure 2C:
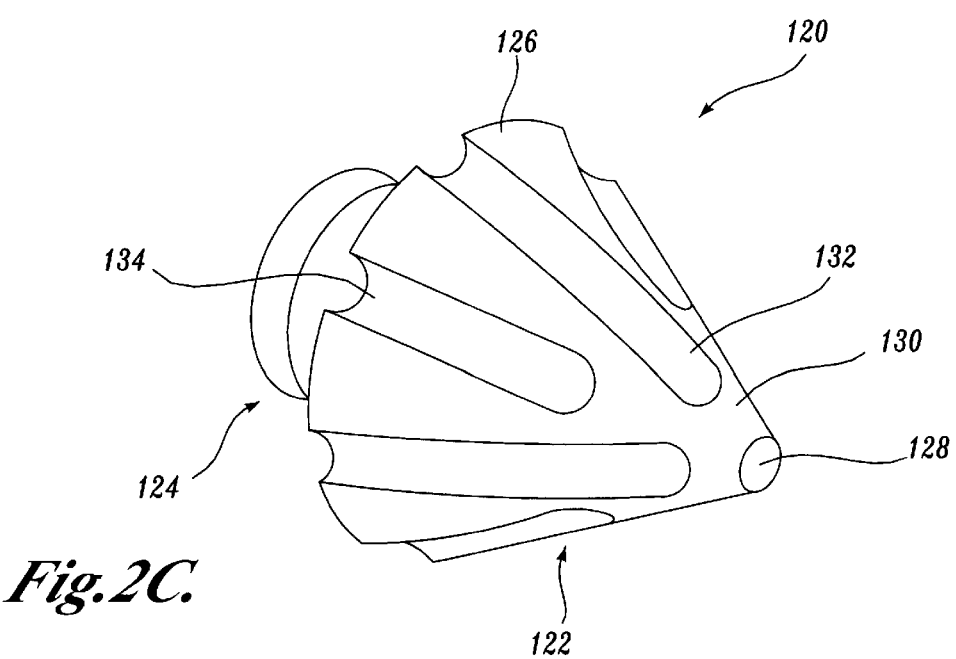

FIGS. 2A–2C illustrate various embodiments of an ablation burr 52 constructed according to the present invention. Unlike conventional ablation burrs that have a relatively uniform outer surface that is covered with an abrasive material, such as diamond grit, the ablation burrs of the present invention are designed to move ablated material and liquid proximally to an aspiration lumen and/or direct fluid in the vessel radially outward towards the interior vessel wall in order to provide a scouring effect as the burr is rotated. As shown in FIG. 2A, the ablation burr 80 includes a distal portion 82 and a proximal portion 84. The proximal portion 84 is a cylinder of a generally uniform diameter which is less than the maximum diameter of the ablation burr 82. The distal portion 84 of the burr has a maximum diameter at the point where the distal portion 82 meets the proximal portion 84. The diameter of the distal portion tapers down gradually to the distal tip of the burr such that the distal portion has an ovoidal shape. The ablation burr 80 includes a central lumen 86 through its longitudinal axis in which the guide wire may be routed.

Unlike conventional burrs, the ablation burr 80 includes one or more channels 88 that are machined into the outer surface of the burr that operate to move ablated material and liquid proximally as the burr is rotated by a driveshaft. These channels 88 may extend along the length of the burr. Alternatively, some channels, such as a channel 90, may extend along only a portion of the length of the burr. In the embodiment shown, the channel 90 begins at approximately the distal tip of the burr and continues proximally for about one third of the length of the distal portion 82 of the burr. The purpose of the truncated channel 90 is to direct fluid and ablated material radially outward as the ablation burr 80 is rotated. The direction of fluid radially outward has the effect of scouring the internal vessel wall to further remove occluding material from the vessel. The area 91 of the distal portion 82 that is between the channels 88 and 90 is coated with an abrasive material such as a diamond grit. As will be appreciated by those skilled in the art, the ablation burr 80 may have all the channels run the length of the burr, have all the channels extend only a portion of the length of the burr, or contain some combination thereof.

FIG. 2C shows another alternative embodiment of an ablation burr according to the present invention. Here, the ablation burr 92 includes a distal portion 94 and a proximal portion 96. The distal portion 94 has a point of maximum diameter 98 which tapers gradually to the distal tip 100 of the burr. The difference between the burr 92 shown in FIG. 2C and the burr 80 shown in FIG. 2A is that instead of the diameter of the burr changing sharply where the distal portion of the burr meets the proximal portion, the diameter decreases gradually in an area 102 that joins the proximal and distal portions of the burr. This area 102 includes one or more channels 104 that operate to direct fluid radially outward as the burr 92 is rotated. Again, the burr may include a number of channels 104 that extend the entire length of the burr or channels 106 that extend a portion of the length of the burr to direct ablated material proximally towards an aspiration lumen and/or radially outwards. An outer surface 108 of the distal portion 94 of the burr is preferably coated with an abrasive material to abrade deposits in the vein graft.

FIG. 2C shows yet another embodiment of an ablation burr 120 according to the present invention. The ablation burr 120 includes a distal portion 122 and a proximal portion 124. The proximal portion 124 is a cylinder having a uniform diameter whereas the distal portion 122 has a point of maximum diameter where the distal portion 122 meets the proximal portion 124. The diameter of the distal portion 122 decreases linearly to the distal tip 128 of the burr thereby providing the distal portion 122 with a generally conical shape. The outer surface 130 of the distal portion of the burr is coated with an abrasive material in order to abrade material in the vessel as the burr 120 is rotated.

As with the burrs shown in FIGS. 2A and 2B, the ablation burr 120 includes one or more channels 132, 134 in the outer surface 130 of the burr. In this embodiment, each of the channels along the outer surface of the burr is relatively straight, however, spiral channels could also be used.

Figure 3A:
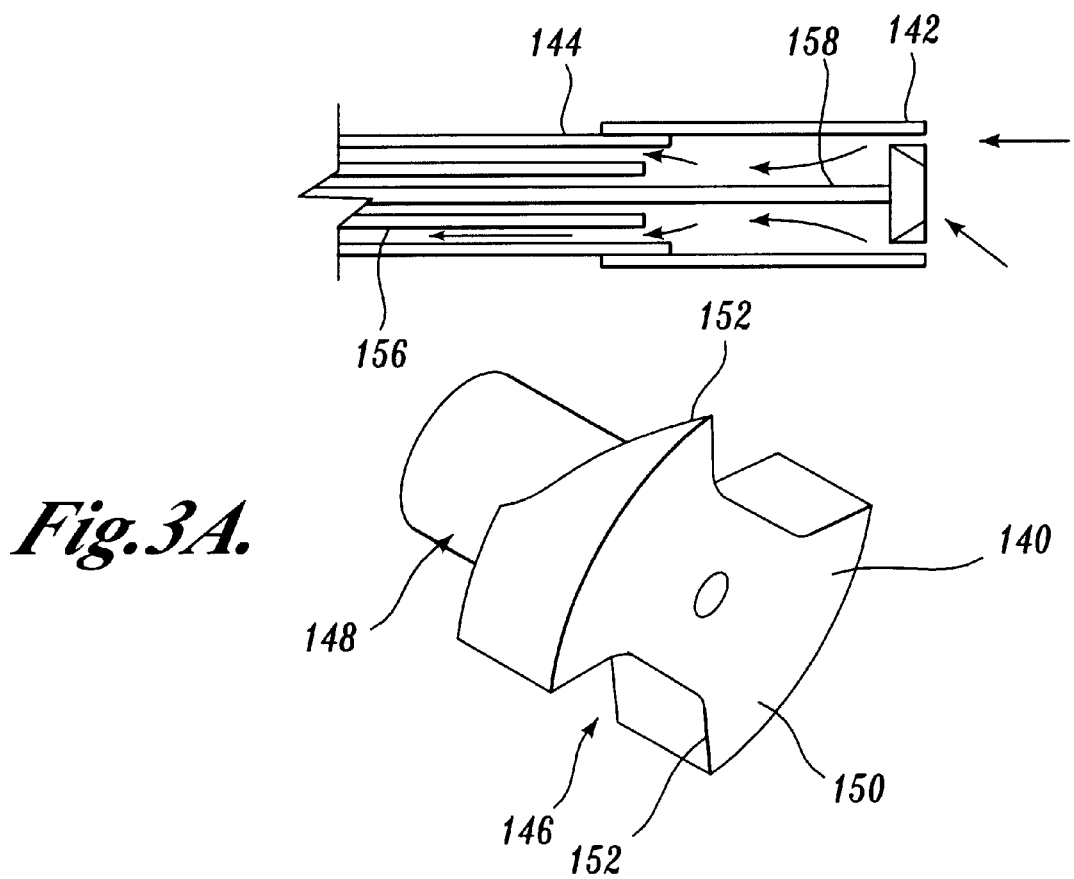
FIGS. 3A–3B illustrate alternative ablation burrs having a generally flat distal face and a number of blades that move ablated material proximally when rotated in accordance with another aspect of the present invention.
Figure 3B:
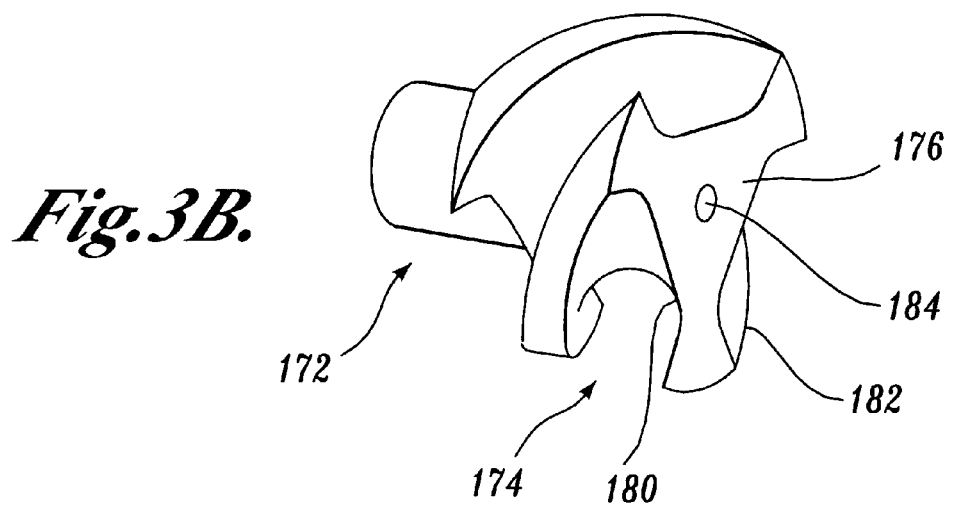

FIGS. 3A–3B illustrate an alternative ablation burr 140 according to another aspect of the present invention. The ablation burr 140 is designed to remain within a protective shroud or sheath 142 secured to the distal end of the guide catheter 144. The ablation burr 140 has a distal portion 146 and a proximal portion 148. The proximal portion 148 comprises a cylinder having a diameter that is smaller than the maximum diameter of the distal portion 146. The distal portion 146 comprises a disk with a diameter larger than that of the proximal portion and a flat distal surface 150. The flat distal surface 150 has an abrasive coating thereon that abrades occluding material from the vessel as the ablation burr 140 and guide catheter 144 are advanced through the vessel. Extending proximally from the flat distal surface 150 are one or more blade surfaces 152. The blade surfaces 152 act as propellers to push liquid and ablated material from the distal surface 150 towards an aspiration lumen which is located near the proximal end of the burr. In the embodiment of the invention shown in FIG. 3A, the aspiration lumen is formed between the guide catheter 144 and a sheath 156 that surrounds a driveshaft 158 that rotates the ablation burr 140.

FIG. 3B shows an alternative embodiment of the ablation burr shown in FIG. 3A. The ablation burr 170 includes a proximal portion 172 and a distal portion 174. The proximal portion 172 is a cylinder having a radius that is smaller than the maximum radius of the ablation burr 170. The distal portion 174 comprises a disk having a flat distal surface 176 that may include an abrasive material to abrade occluding matter from a vessel as the ablation burr 170 is rotated. The ablation burr 170 includes three serpentine blade surfaces 178, 180, 182 that extend from the distal surface 176 to the point where the proximal portion 174 of the burr meets the distal portion 172 of the burr. Each of the blade surfaces 178, 180, 182 operates to move ablated material proximally as the ablation burr 70 is rotated by a driveshaft.

The ablation burr 170 may include a central lumen 184 so that the ablation burr can be routed over a guide wire (not shown) if desired.

FIG. 3C illustrates yet another embodiment of an ablation burr according to the present invention. The ablation burr 185 has an ellipsoidal distal half 186 that is covered with an abrasive material. A proximal section 187 comprises a generally cylindrical section having a diameter less than the diameter of the proximal section 186. A drive shaft (not shown) is secured to the proximal section 187 to rotate the burr. The proximal section 187 includes a number of blades 188 disposed around the cylindrical section. Each blade has a radius that is less than the radius of the distal section 186. In operation, the distal section remains outside a surrounding sheath while the blades 188 remain in the sheath and move ablated material and liquid proximally when the burr 185 is rotated by the drive shaft.

FIG. 4 illustrates an alternative embodiment of an ablation burr according to the present invention. The ablation burr 190 has a generally "auger"-shaped configuration with a proximal portion 192 and a distal portion 194. The proximal portion 192 comprises a cylinder having a maximum diameter that is less than the maximum diameter of the distal portion 194. The distal portion generally comprises a cylinder having a radius larger than the radius of the proximal portion 192 and a channel 196 that spirals along the length of the distal portion 194. The channel 196 operates to move ablated material and liquid proximally as the burr 190 is rotated. If desired, at least a portion of the leading surface of the ablation burr 190 is coated with an abrasive material to aid the removal of occluding material from the vessel as the ablation burr 190 is rotated.

Figure 5A:
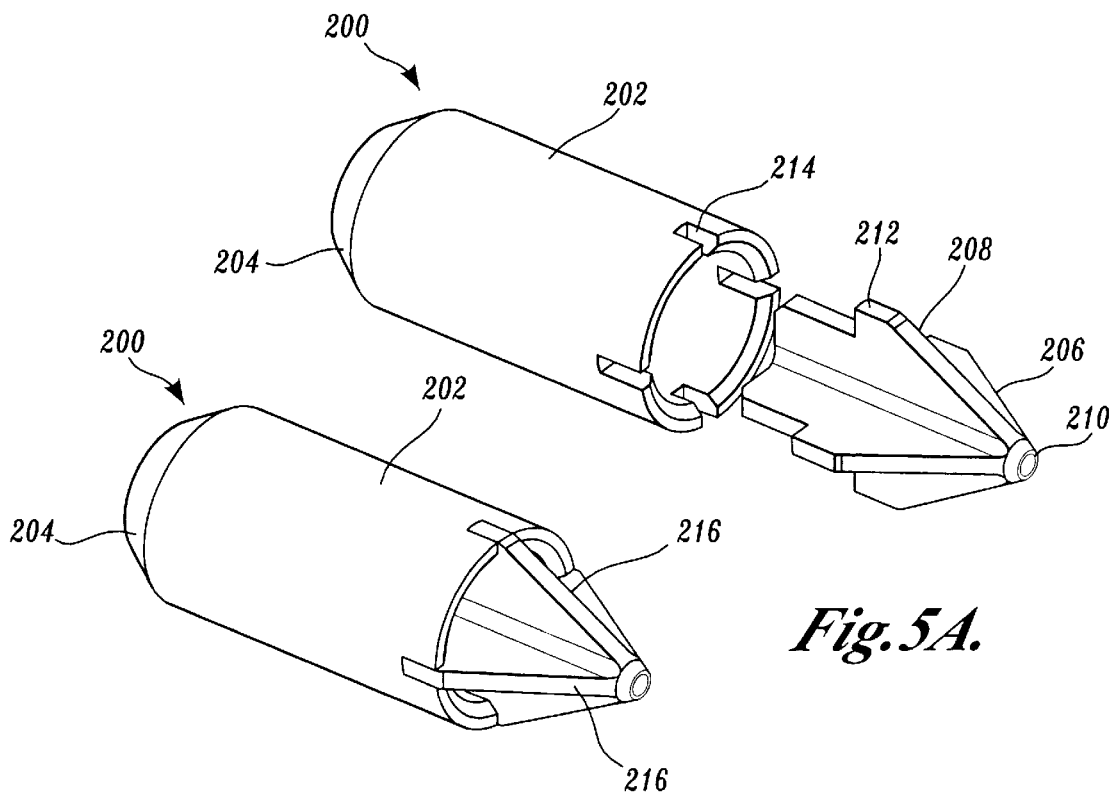
FIGS. 5A–5B illustrate alternative embodiments of a canister burr in accordance with another aspect of the present invention.
Figure 5B:
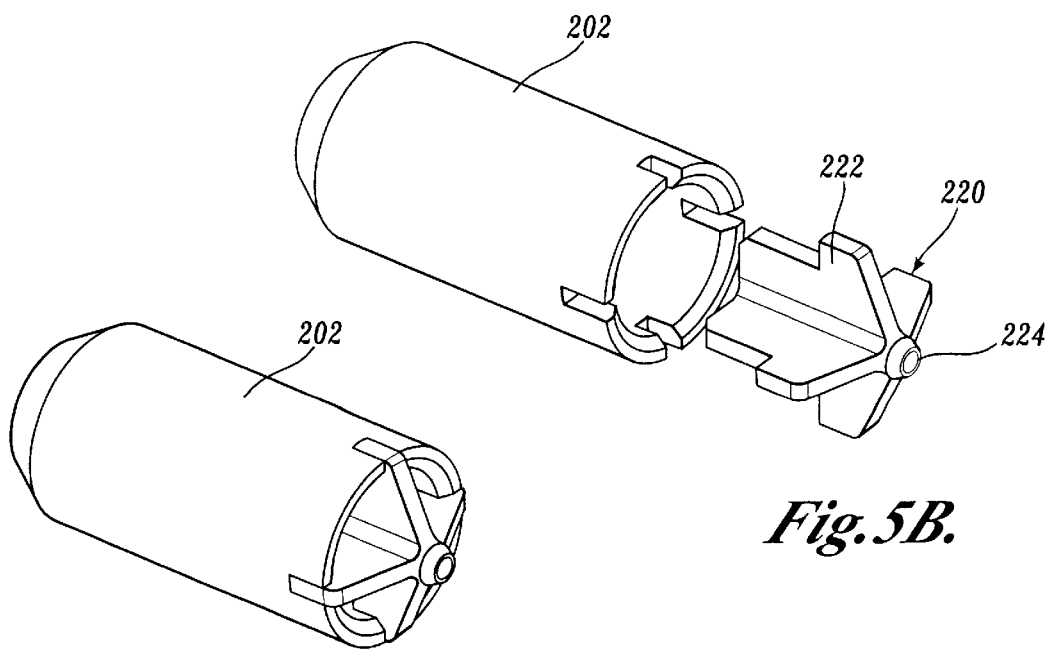

FIGS. 5A and 5B show alternative embodiments of an ablation burr according to the present invention. As shown in FIG. 5A, an ablation burr 200 comprises a cylinder 202 having generally smooth sides and a tapered proximal end 204 into which a driveshaft is secured. A blade cluster 206 is fitted within the cylinder 202. The blade cluster 206 comprises a series of generally flat blades 208 that are equally spaced around and extend radially outward from a central lumen 210. The proximal end of the blades 208 has a diameter selected to engage the inner wall of the canister 202. Each of the blades 208 also include an outwardly extending notch that fits within a corresponding slot 214 on a distal rim of the canister 202. The distal end of the blades 208 extend outwardly from the distal end of the canister 202 and taper down to the distal end of the blade cluster. With the blade cluster 206 secured in the canister 202 via an adhesive or by welding, the blade cluster 206 divides the interior lumen space of the canister 202 into a series of longitudinally extending sections through with particles may be aspirated. If desired, the outer surface of the blades that extend from the distal end of the canister 202 may include an abrasive material to aid in ablating material from a vessel lumen.

FIG. 5B shows an alternative embodiment of the ablation burr shown in FIG. 5A. Again, the ablation burr includes a canister 202 in which a blade cluster 220 is inserted. The blade cluster includes a number of radially extending blades 222 that are equally spaced around a central lumen 224. The difference between the blades 222 shown in FIG. 5B and the blades 208 shown in FIG. 5A is that the distal end of the blades do not extend as far from the distal end of the canister 202.

FIG. 6 shows yet another embodiment of an ablation burr according to the present invention. The ablation burr 240 comprises a "dumbbell"-shaped device comprising a distal lobe 242 and a proximal lobe 244 wherein the distal lobe and proximal lobe are joined by a center section 246. An aspiration port 248 within the center section 246 is in fluid communication with a lumen that extends through the burr 240 and provides a port through which ablated particles can be aspirated. In a current embodiment of the invention, the burr 240 is rotated by a sealed driveshaft250 connected to the proximal end of the burr. Particles and fluid aspirated into the port 248 are carried in a lumen within the sealed driveshaft to a collection jar that is external to a patient. If desired, a portion of the distal lobe 242 may be coated with an abrasive 252 to aid in ablating material from a vessel lumen. It is believed that when rotated, each of the bulbs 242, 244 will push liquid radially outward towards a vessel wall thereby creating a region of high pressure. The center section of the burr area 246 between the distal and proximal bulbs forms an area of low pressure such that ablated material and liquid will be drawn into the aspiration port 248 for removal from the vessel.

FIG. 7 illustrates another embodiment of an ablation burr 260 according to the present invention. The ablation burr 260 comprises a "bell"-shaped tube having a large central lumen that expands in diameter at a flared distal end 262 of the burr. A proximal end 264 of the burr comprises a cylinder having a diameter less than the maximum diameter of the distal end 261 of the burr. The proximal end 264 is designed to be coupled to a driveshaft that rotates the burr. The proximal end 264 of the burr is coupled to the distal end by two of more legs 268. Spaces between the legs 268 expose the lumen in the center of the burr. In operation, the majority of the distal end 261 fits within a surrounding guide catheter 272. Only the flared distal end 262 of the ablation burr extends from the distal end of the guide catheter. The leading surface of the distal end 262 may be coated with an abrasive or other material to aid in removing matter form the vessel lumen. In operation, when a vacuum source is connected to the maximal end of the burr, aspirated particles are drawn into the flared end and through the interior lumen of the burr where they are carried away by an aspiration lumen.

FIGS. 8A and 8B show yet another alternative embodiment of an ablation burr according to the present invention. The ablation burr 280 comprises a conventional ellipsoidal shaped burr having a central lumen 282 disposed therein in which the driveshaft is fitted to secure it to the burr. In addition, a guide wire can be routed through the central lumen 282 and out the distal end of the burr. A plurality of holes 284 are positioned around the outer surface of the distal half of the burr. Each hole extends from the outer surface of the burr into the central lumen. When used with a sealed driveshaft to rotate the burr, vacuum is applied and obstructing material is drawn into the holes 284, while the rotation of the ablation burr causes particles to be sheared off from the vessel wall. The ablated particles may be drawn into the central lumen 282 of the ablation burr 280 and aspirated out the center of the hollow driveshaft. Alternatively, the particles may be aspirated outside of the driveshaft.

An alternative to the embodiment shown in FIG. 8A is the ablation burr 290 shown in FIG. 8B. Again, the ablation burr includes a hollow lumen 292 in which the driveshaft is secured and through which a guide wire can be extended. In this embodiment, the holes 294 on the outside surface of the distal half of the burr extend radially inward to a pair of inner lumens 296 that extend along the length of the burr but are radially displaced from the central lumen 292. Each of the lumens 296 terminates at a fitting 298 that fits within a corresponding lumen 300 of a connected catheter 302. Vacuum is applied to the lumens 300 so that aspirated particles are drawn through these lumens instead of the central lumen of the catheter through which the driveshaft extends. Using this embodiment, the catheter 302 rotates with the ablation burr 290 as the burr is used in the vessel.

Figure 9A:
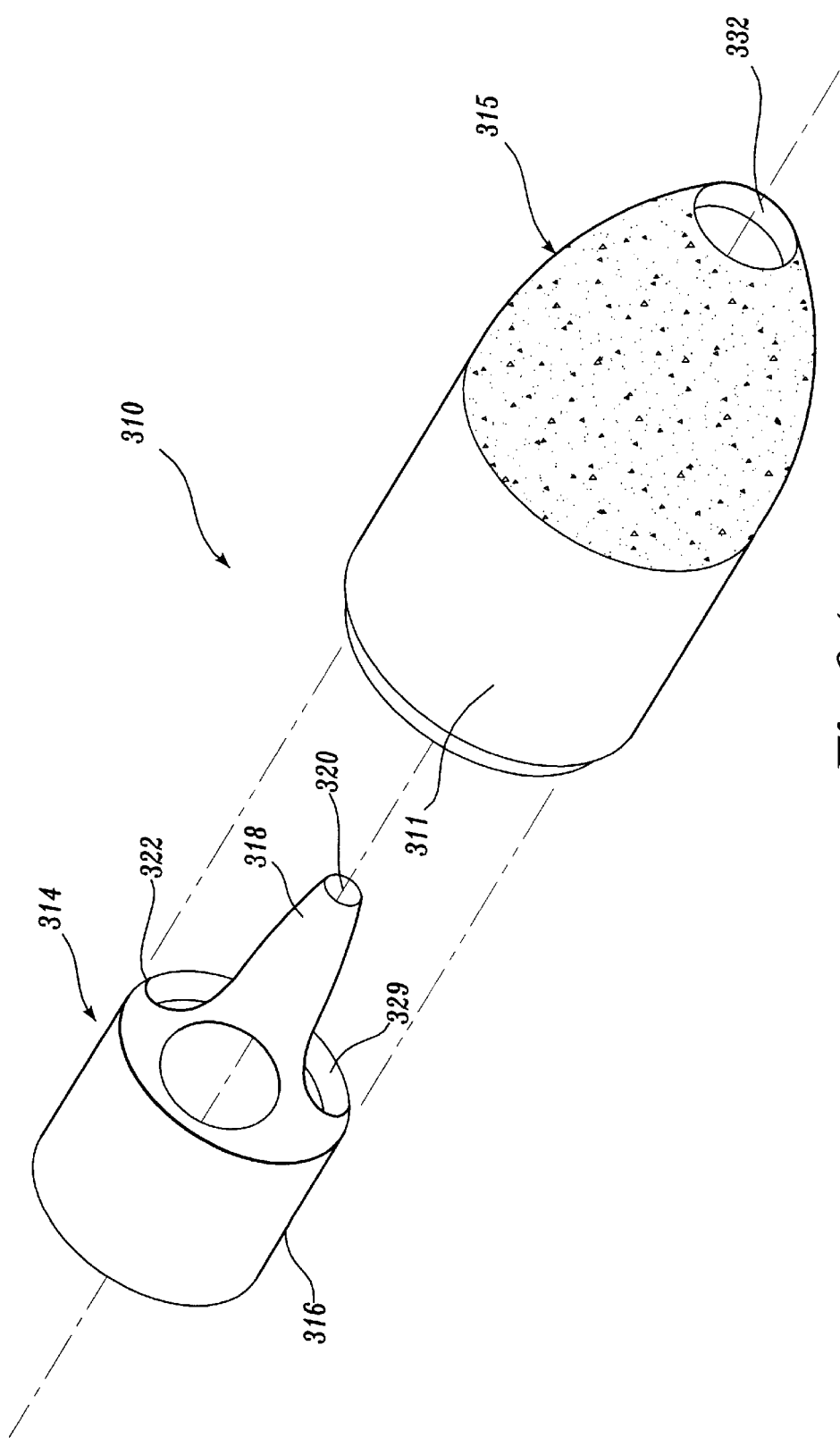
FIGS. 9A–9B illustrate an ablation burr that directs ablated material and liquids proximally in accordance with another aspect of the present invention.

FIG. 9A shows yet another alternative embodiment of an ablation burr according to the present invention. The ablation burr 310 comprises an outer shell 312 and an inner core 314. The outer shell 312 comprises a generally cylindrical proximal section 311 and a distal section 315 which tapers in diameter to form an ovoidal tip. The tapered section may be covered with an abrasive or other material that aids in ablating material from a vessel wall. At the distal end of the burr is an opening 332 that is larger than the diameter of a guide wire (not shown) over which the burr may be routed. The inner core 314 comprises a cylindrical proximal section 316, and a tapered nose section 318 having a lumen 320 disposed therein, through which a guide wire can be passed. The nose section 318 may also be covered with an abrasive grit on its outer surface. The diameter of the nose section 318 is substantially smaller than the diameter of the proximal section 316. The nose section 318 is joined to the cylindrical proximal section 316 via a concave transition region 322 having a number of holes 324 disposed around its circumference.

The proximal section 316 of the core is secured to the inner diameter of the proximal section 311 of the shell 312 such that both the core and shell rotate together with a driveshaft that is secured within the inner core.

Figure 9B:
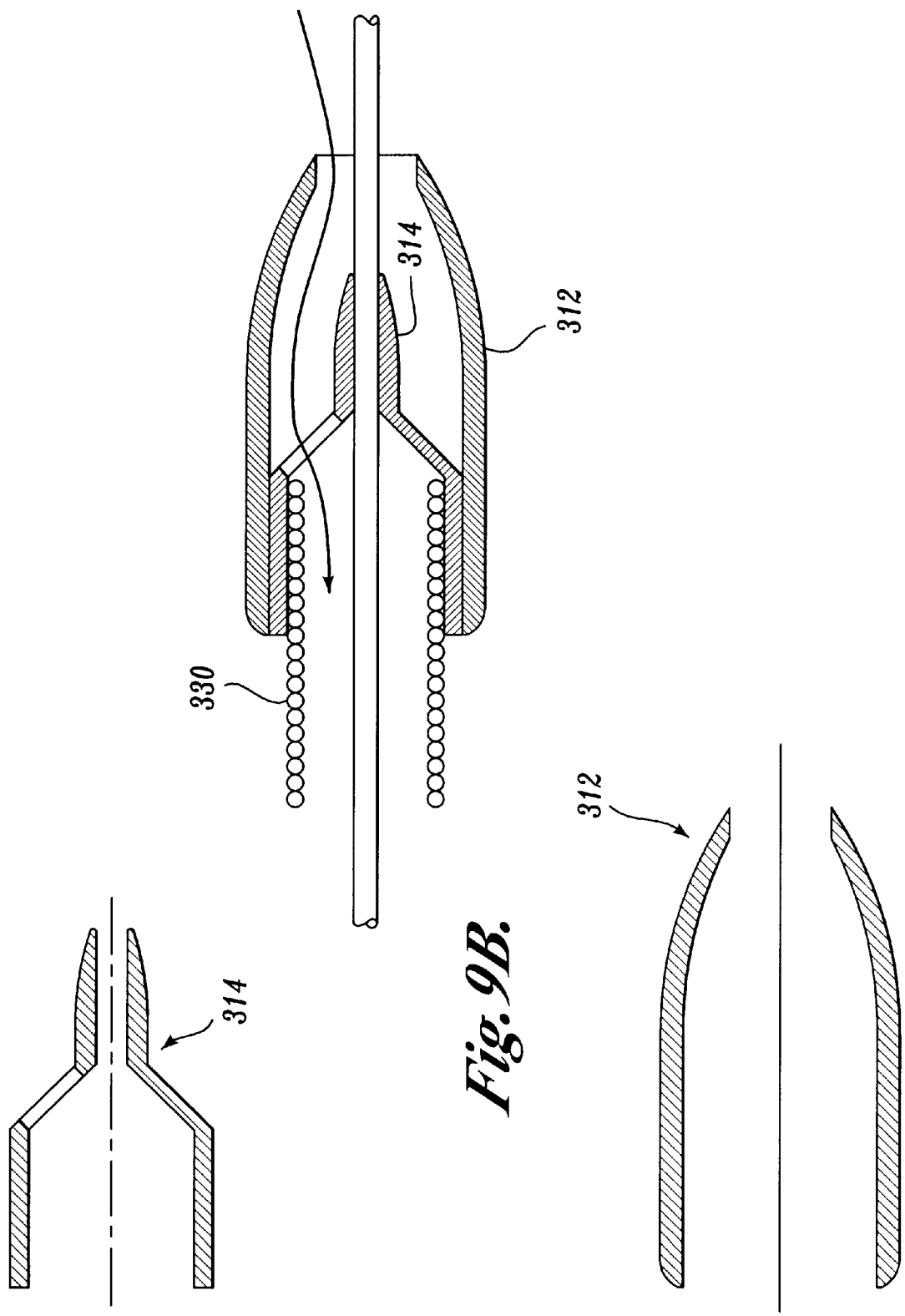

As shown in FIG. 9B, when the burr 310 is rotated by a sealed driveshaft 330, fluid enters the opening hole 332 at the distal end of the shell. Fluid and ablated material are pushed radially outward when forced between the tapered nose section 318 and the inner wall of the distal section 315 of the outer shell 312.

The fluid and ablated material are forced through the holes 324 and proximally through a sealed driveshaft 330.

In some instances, it may be desirable that an ablation burr remain a fixed distance from the distal end of a sheath that surrounds the driveshaft. In that case, a coupler as shown in FIGS. 10A and 10B can be used. The coupler 350 comprises a generally cylindrical rod having a threaded proximal end 352 that mates with corresponding threads on the distal end of a sheath 372 or to another securing mechanism. The coupler 352 is generally hollow and includes one or more aspiration ports 354 along its length so that aspirated material can be drawn into the coupler. The coupler has a hole 356 at its distal end with a diameter that is less than the inner diameter of the coupler section 350.

To secure the ablation burr to the coupler, a post 360 is provided. The post has a lumen therein in which a driveshaft is secured. The post 360 has a shaft 362 having a diameter that will fit through the hole 356 at the distal end of the coupler. A proximal cap end 364 of the post 360 has a diameter that is greater than the diameter of the hole 356 in the distal and of the coupler such that the proximal end of the post forms a bearing surface with the inner surface of the end of the coupler section. When the post 360 is inserted into the coupler, the shaft 362 extends out of the hole 356 and an ablation burr 370 is secured to the shaft 362. As shown in FIG. 10A, the coupler 350 is threaded onto the end of a sheath 380. Vacuum applied to the sheath 372 draws material in through the aspiration ports 354 and down the passageway extending on the outside of the driveshaft and the inside of the sheath 380.

Figure 11:
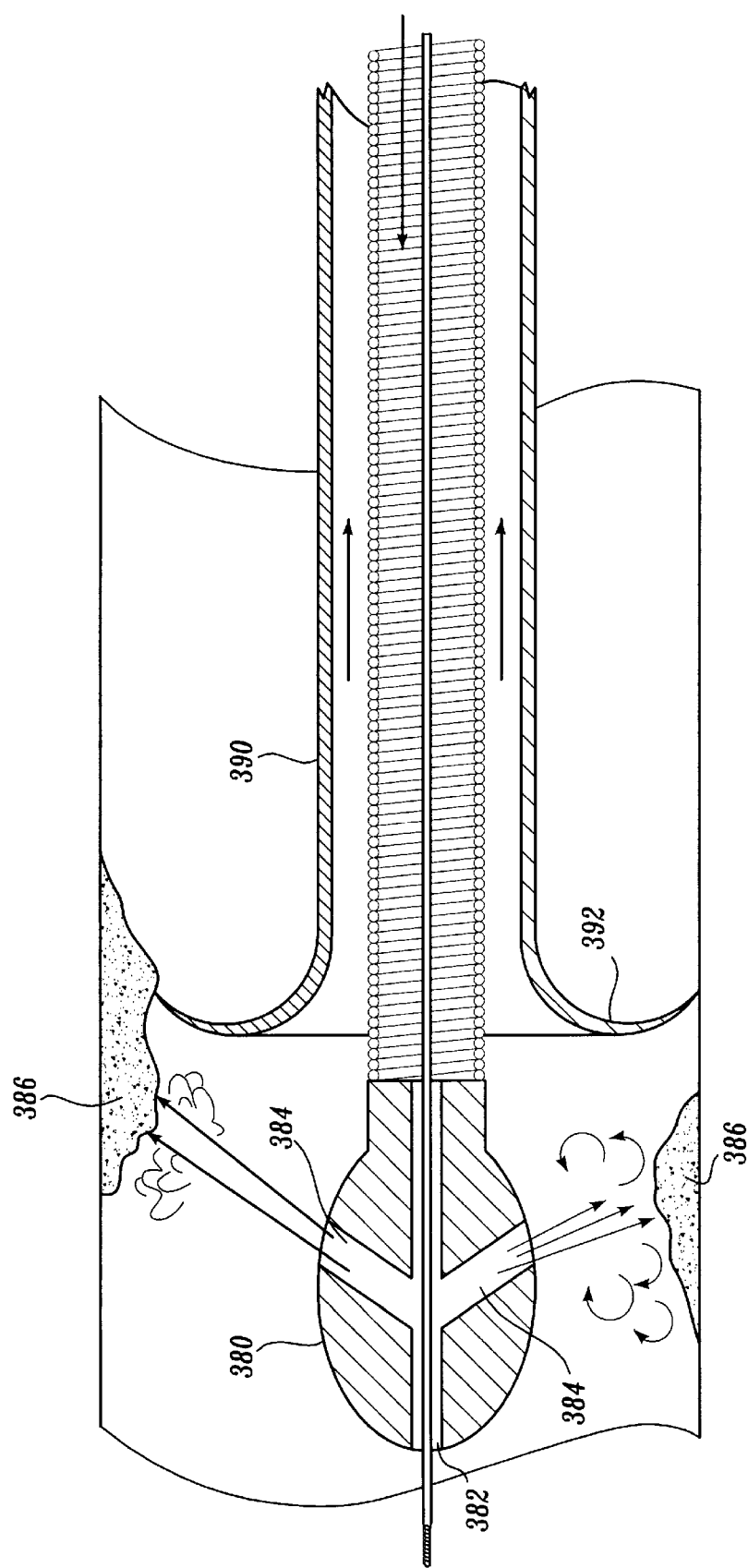
FIG. 11 illustrates an ablation burr having fluid ports that direct an infusion fluid towards an interior vessel wall to aid in material removal.

In some instances, it may be desirable to infuse liquid into the treatment area. Such liquid may be infused either to maintain vessel pressure or to aid in the removal of material from a vessel wall. In that case, an ablation burr of the type shown in FIG. 11 may be desirable. The ablation burr 380 includes a central lumen 382 and one or more ports 384 in fluid communication with the central lumen 382. The ports 384 are directed radially outward and to the rear of the burr. When rotated by a sealed driveshaft, liquid can be pumped through the driveshaft and out the ports 384. Fluid jets exiting the ports 384 aid in the removal of material 386 disposed on the vessel wall.

To prevent the infused liquid from being forced out the distal end of the burr, the hole at the distal end of the burr is only slightly larger than the diameter of the guide wire that extends through the hole.

Figure 11A:
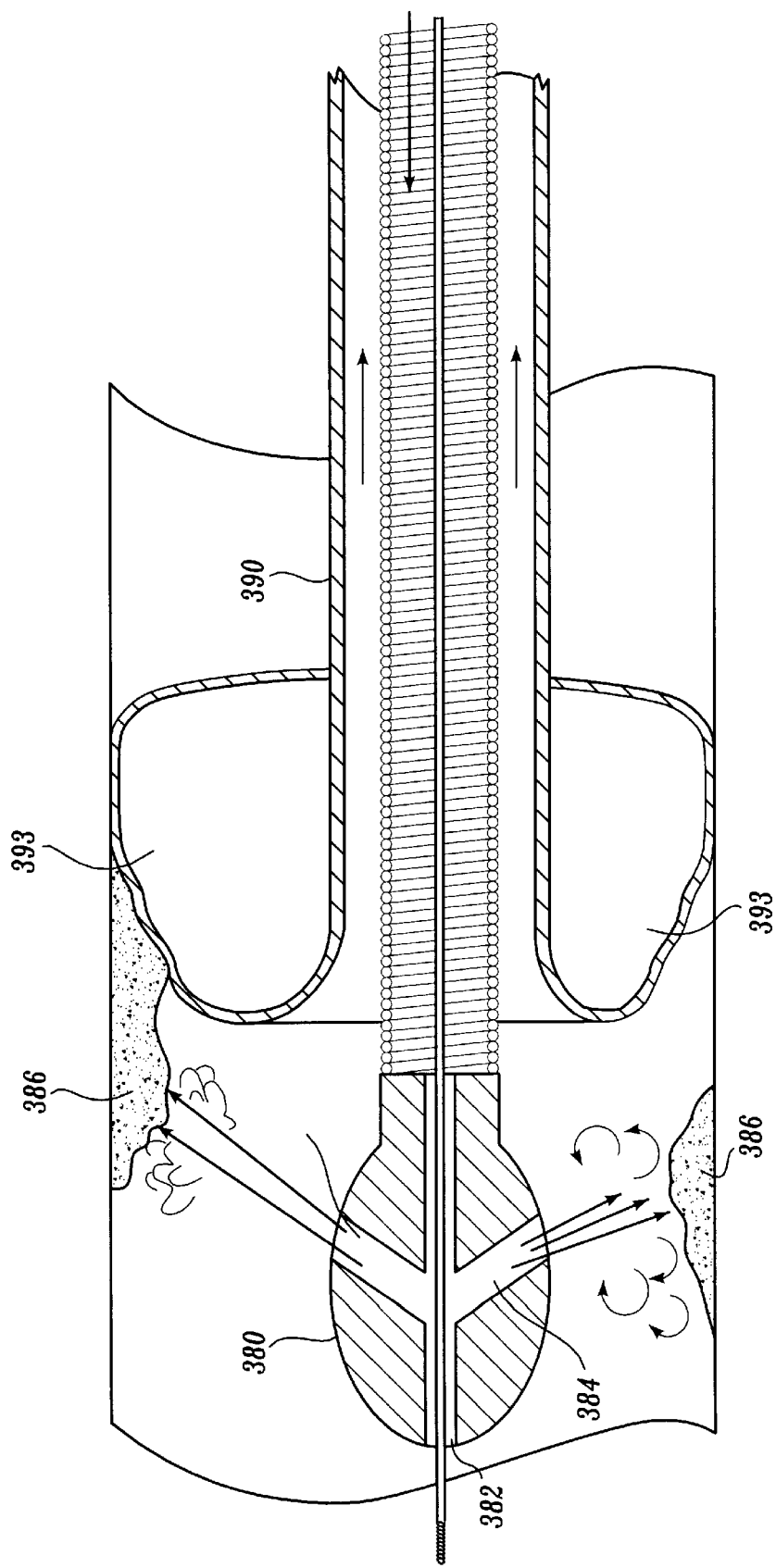
FIG. 11A illustrates an embodiment of the invention including an occlusion balloon on the distal end of a sheath that is inflated to seal a treatment.

To aid in the aspiration of the ablated material 368, a sheath 390 may surround the driveshaft. The distal end of the driveshaft may include a flared section 392 that expands radially outward to seal the vessel and aid in guiding ablated material into the aspiration lumen. The flared section 392 can be made of flexible polymeric material. Metallic mesh or wires can be used to support the flared section. The flared section 392 is attached to the distal end of the aspirating sheath. This flared section is either folded against the sheath 390 or extended forward of the sheath when pushed through the guiding catheter. It will expand radially once it exits the guiding catheter to aid aspirating. Another design to aid aspirating is to use an occlusion balloon instead of the flared section. As shown in FIG. 11A, an occlusion balloon 393 is mounted on the distal tip of the sheath 390. The balloon 393 can be inflated to block the vessel once the sheath 390 is situated in the vessel.

Figure 12:
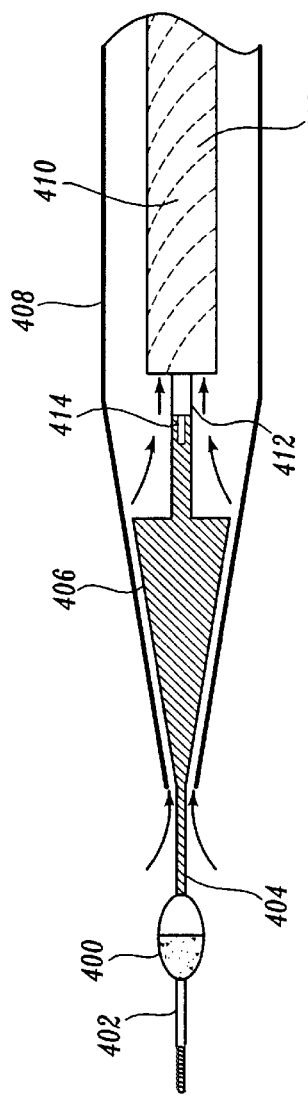
FIG. 12 illustrates a driveshaft having a conical section near its distal end to pump ablated material and liquid proximally when rotated in accordance with yet another aspect of the present invention.

Another mechanism for aiding in the aspiration of ablated material from a vessel is shown in FIG. 12. Here, an ablation burr 400 is disposed over a guide wire 402. The ablation burr 400 is driven by a driveshaft 404 having a conical, tapered section 406 near the distal end of the driveshaft. The conical section 406 expands in diameter from a point near the ablation burr and extending in the proximal direction. At the proximal end of the conical section 406, the diameter of the driveshaft returns to the diameter of its distal tip. The conical section 406 is preferably secured to a conventional driveshaft with a hypo tube coupler 414. A guide catheter 408 surrounding the driveshaft has a similarly shaped tapered section 410 that surrounds the conical section 406 of the driveshaft. Liquid entering the area between the conical section 406 of the driveshaft and the tapered section of the guide catheter 408 is pushed radially outward by the movement of the driveshaft, thereby forcing the liquid proximally where it can be aspirated either through a sheath 410 surrounding a proximal portion of a driveshaft 412, or in the lumen created between the sheath 410 and the guide catheter 408.

To aid in the movement of ablated material proximally, the inner surface of the sheath 410 may include spiral channels 416 or other mechanisms such as blades, etc. that aid in directing ablated material and liquid proximally along the length of the lumen created between the outside of the sheath 410 and the inside of the guide catheter 408. Alternatively, the inside walls of the guide catheter 408 may include spiral channels (not shown) to aid in the movement of ablated material proximally if the catheter is used with a sealed driveshaft or other catheter that rotates within the guide catheter 408.

Figure 13A:
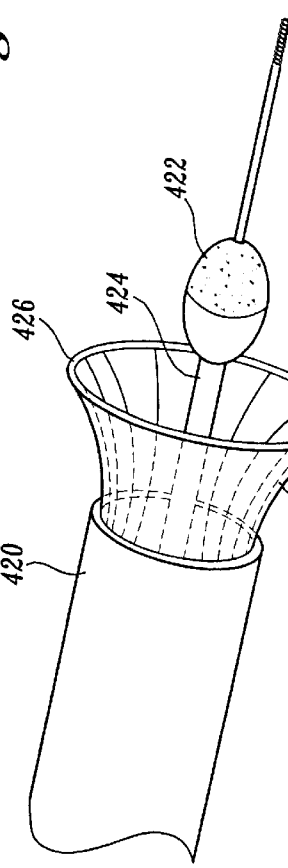
FIGS. 13A–13B illustrate two embodiments of an expandable sleeve that fits within a sheath catheter to seal a proximal end of a treatment site in accordance with another aspect of the present invention.
Figure 13B:
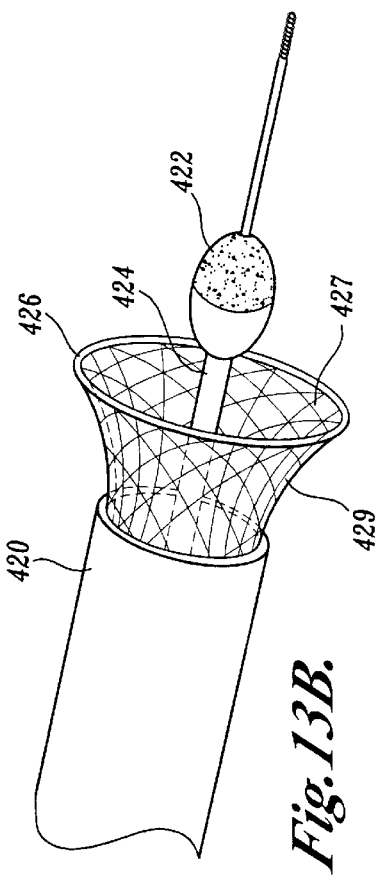

As indicated above, it is sometimes necessary to seal the proximal end of a treatment area in order to guide ablated material into an aspiration lumen or prevent it from escaping in the bloodstream. As shown in FIG. 13A, a sheath 420 surrounds an ablation burr 422 that is driven by a driveshaft 424. Disposed between the sheath 420 and the driveshaft 424 is a lining 426 having a distal end that expands radially when advanced out the distal end of the sheath 420. The expanded end of the lining 426 seals against the vessel wall in which the sheath is located in order to prevent ablated material from flowing proximally and to guide such ablated material into an aspiration lumen. The lining 426 is composed out of thin flexible polymer film 427 with resilient frame 428. The frame 428 can be made as a group of parallel strands as shown in FIG. 13A, or as a net 429 as shown in FIG. 13B. In closed state, lining 426 is collapsed within the sheath 420. Once the lining 426 is extended from the tip of the sheath 420, the frame 428 or net 429 causes expansion of the lining 426.

Figure 14:
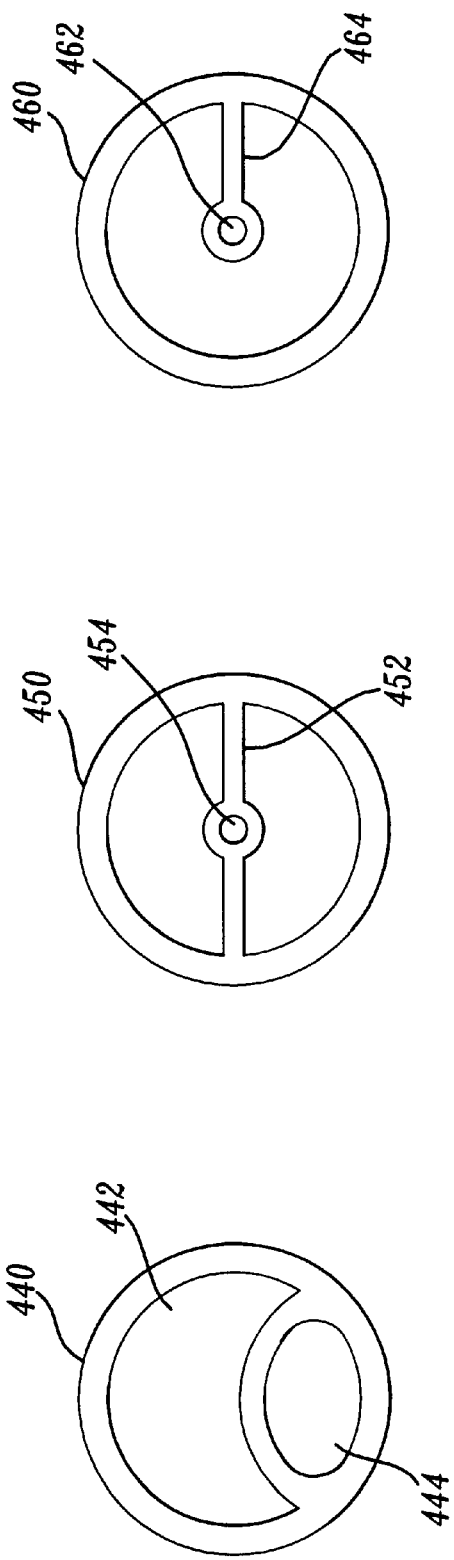
FIG. 14 illustrates alternative multi-lumen catheter designs that may be used with the aspirating ablation system of present invention.

In most of the examples described above, the aspiration lumen comprises the space between the driveshaft and the surrounding sheath. However, in some instances, it may be desirable to use a multi-lumen sheath. One lumen is used to route the guide wire and driveshaft of the ablation burr. Another lumen is used for aspiration. FIG. 14 shows cross-sections of three different multi-lumen catheters designs that can be used in accordance with the present invention. A catheter 440 includes a large lumen 442 and a smaller lumen 444. Either lumen can be used for aspiration or routing the ablation driveshaft and guide catheter.

A catheter 450 is divided in the middle by a median strip 452. The center of the median strip 452 is slightly larger to accommodate a central lumen 454 through which a guide catheter and/or driveshaft can be routed. The lumens created on either side of the median strip 452 can be used for aspiration or fluid infusion.

A catheter 460 has a central lumen 462 that is disposed on a post 464 that extends from the inner wall of the catheter 460. Each of the catheter designs shown in FIG. 14 can be extruded using known techniques. With a multi-lumen design, both aspiration and infusion can be used to maintain fluid pressure during the treatment process.

Figure 15A:
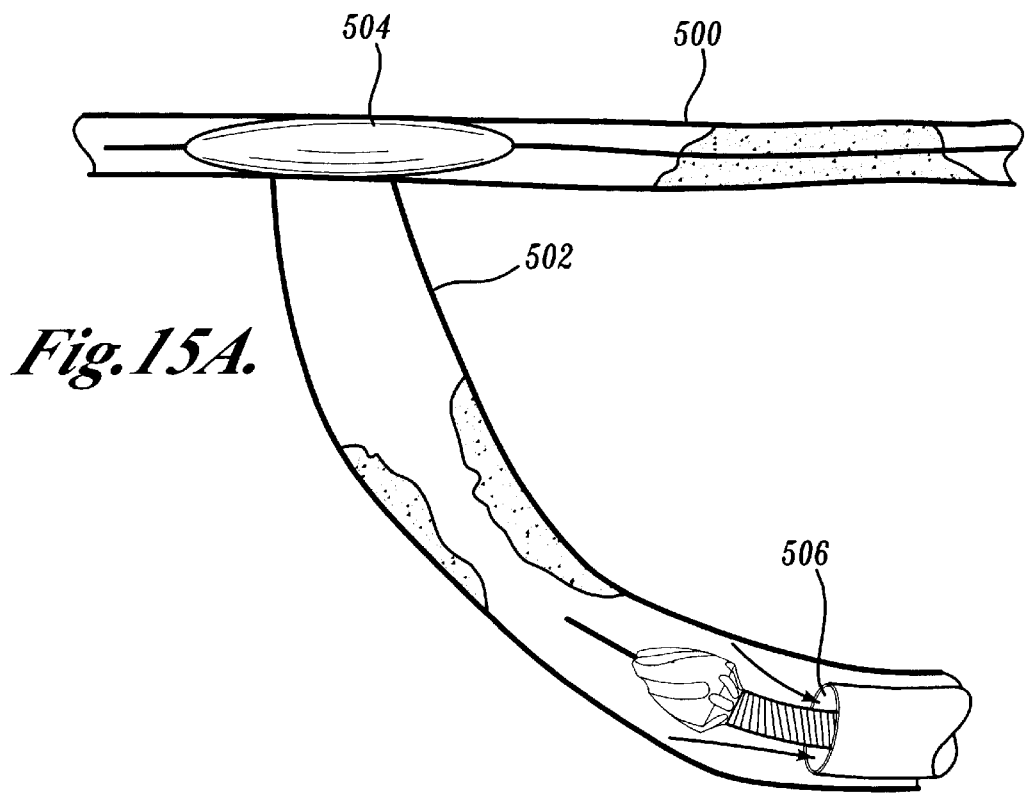
FIGS. 15A–15B illustrate alternative methods of sealing a bypass vessel or native coronary vessel prior to ablation treatment.
Figure 15B:
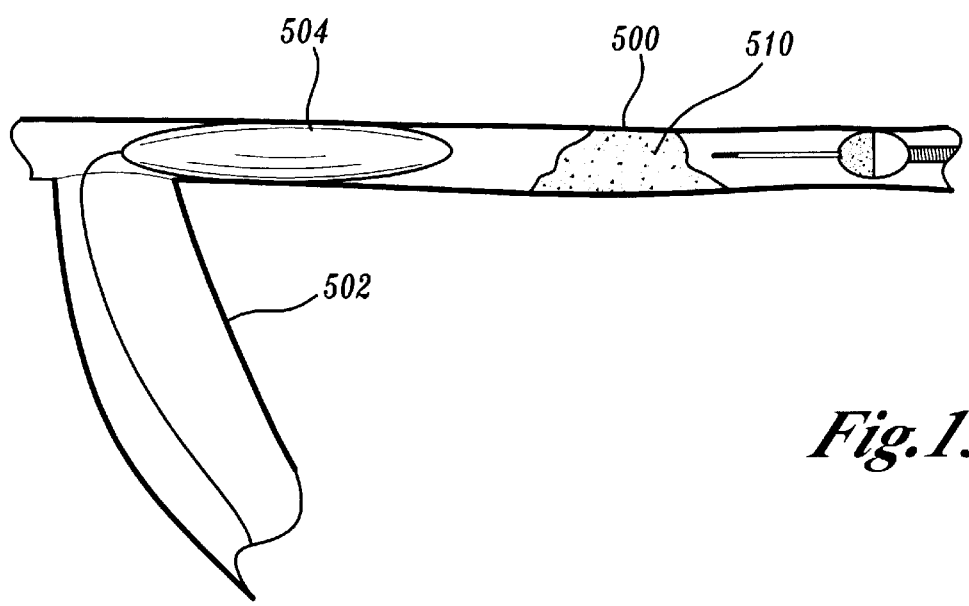

As indicated above, it is sometimes necessary to isolate a treatment area prior to ablating material from a vein graft. FIG. 15 shows one technique whereby a balloon catheter can be routed through a native coronary vessel 500. When positioned at the junction of the bypass vessel 502 and the native vessel 500, the balloon 504 can be expanded to seal the distal end of the bypass vessel. With the distal end sealed, treatment can take place whereby ablated material is drawn into an aspiration lumen 506 within the vessel being treated.

An alternative approach to the treatment of coronary vessels is to route a balloon catheter through the bypass vessel 502 and distal to an original blockage 510 within the native coronary vessel 500. Using more modern techniques such as atherectomy, it is now possible to treat the original blockages that may not have been treatable when the bypass vessel was installed. A balloon 504 on the distal end of the balloon catheter is inflated distal to the original blockage, an ablation burr or other medical device is advanced through the original blockage 510. Depending upon the likely composition of the blockage material, the ablated material can be aspirated in the manner described above. With the original blockage treated, it is possible that the patient would have two vessels through which blood can flow to the heart muscle.

While the preferred embodiment of the invention has been illustrated and described, it will be appreciated that various changes can be made therein without departing from the scope of the invention. It is therefore intended that the scope of the invention be determined from the following claims and equivalents thereto.

The embodiments of the invention in which an exclusive property or privilege is claimed are defined as follows:

1. An ablation burr for removing deposits from a patient's vessel, comprising:
   a burr body adapted to be rotated by a driveshaft, at least a portion of the burr body having an abrasive surface;
   the burr body further including a lumen extending at least partially through the burr body, a proximal and distal radially expanded portion and a middle region between the distal and proximal radially expanded portion having a diameter that is everywhere less than the diameter of the proximal and distal portion, the middle region further including an aspiration port in fluid communication with the lumen in the burr body.

2. The ablation burr of claim 1, wherein the drive shaft that rotates the burr body is sealed.

3. The ablation burr of claim 1, wherein the burr body creates a low pressure region adjacent to the aspiration port as the burr body is rotated in a vessel.

4. A method of removing deposits from a vessel in a patient's body, comprising:
   advancing an ablation burr into a vessel, the burr having a burr body at least a portion of which has an abrasive outer surface, a lumen extending at least partially therethrough, a proximal and a distal radially expanded portion, a middle region between the proximal and distal radially expanded portion having a diameter that is everywhere less than the diameter of the proximal and distal radially expanded portion and an aspiration port within the middle region that is in fluid communication with the lumen;
   rotating the ablation burr with a driveshaft;
   engaging the rotating burr with deposits in the vessel; and
   aspirating ablated deposits through the aspiration port.

* * * * *

UNITED STATES PATENT AND TRADEMARK OFFICE
CERTIFICATE OF CORRECTION

PATENT NO. : 6,579,298 B1
DATED : June 17, 2003
INVENTOR(S) : T.J. Johnson

It is certified that error appears in the above-identified patent and that said Letters Patent is hereby corrected as shown below:

<u>Title page,</u>
Item [12], Inventor, "Bruneau, et al." should read -- Johnson --
Item [75], Inventors, "Inventors: Rodney J. Bruneau, Kirkland, WA (US); Robert L. Barry, Kirkland, WA (US); Tim J. Johnson, Seatac, WA (US); Casey Torrance, Seattle, WA (US); Dennis Werner, Redmond, WA (US); Andy Uhrberg, Monroe, WA (US); Matthew Hefner, Puyallup, WA (US); Zihong Guo, Bellevue, WA (US); Mark Wyzgala, Bellevue, WA (US); Robert Morley, Redmond, WA (US); Natalya Peskin, Redmond, WA (US); Brian T. Cran, Seattle, WA (US)" should read
-- Inventor: Tim J. Johnson, Seatac, WA (US) --

Signed and Sealed this

Second Day of March, 2004

JON W. DUDAS
*Acting Director of the United States Patent and Trademark Office*